United States Patent
Tanba et al.

(10) Patent No.: US 11,338,271 B2
(45) Date of Patent: May 24, 2022

(54) POROUS CARBON MATERIAL, METHOD FOR PRODUCING SAME, AND CATALYST FOR SYNTHESIS REACTION

(71) Applicant: Dexerials Corporation, Tokyo (JP)

(72) Inventors: Katsuya Tanba, Tokyo (JP); Yoshiharu Okuda, Tokyo (JP); Teiko Kuroda, Tokyo (JP)

(73) Assignee: Dexerials Corporation, Tokyo (JP)

( * ) Notice: Subject to any disclaimer, the term of this patent is extended or adjusted under 35 U.S.C. 154(b) by 0 days.

(21) Appl. No.: 16/965,121

(22) PCT Filed: Jan. 24, 2019

(86) PCT No.: PCT/JP2019/002381
§ 371 (c)(1),
(2) Date: Jul. 27, 2020

(87) PCT Pub. No.: WO2019/163396
PCT Pub. Date: Aug. 29, 2019

(65) Prior Publication Data
US 2021/0039073 A1    Feb. 11, 2021

(30) Foreign Application Priority Data
Feb. 21, 2018 (JP) .............................. JP2018-028503

(51) Int. Cl.
*B01J 21/18* (2006.01)
*B01J 23/44* (2006.01)
(Continued)

(52) U.S. Cl.
CPC .............. *B01J 21/18* (2013.01); *B01J 23/44* (2013.01); *B01J 35/0026* (2013.01);
(Continued)

(58) Field of Classification Search
CPC ........ B01J 21/18; B01J 23/44; B01J 35/0026; B01J 35/0033; B01J 35/1038;
(Continued)

(56) References Cited

U.S. PATENT DOCUMENTS 2,614,107 A * 10/1952 Wender ................... C07C 33/22
549/70
2,799,708 A * 7/1957 Oakley ................... C07C 45/58
568/384
(Continued)

FOREIGN PATENT DOCUMENTS

| CA | 1173816 | 9/1984 |
| CN | 103121674 | 5/2013 |

(Continued)

OTHER PUBLICATIONS

Martina Bejblova et al., "Hydrodeoxygenation of benzophenone on Pd catalysts." Applied Catalysis A: General 296, pp. 169-175. (Year: 2005).*

(Continued)

*Primary Examiner* — Patricia L. Hailey
(74) *Attorney, Agent, or Firm* — Carmody Torrance Sandak & Hennessey LLP

(57) ABSTRACT

A porous carbon material including a porous carbon material having a specific resistance value of 30 Ωcm or less at a packing density of 0.3 g/cc, wherein a mesopore volume (cm³/g) of the porous carbon material as measured by the BJH method is 0.5 cm³/g or greater.

10 Claims, 1 Drawing Sheet

(51) Int. Cl.
*B01J 35/00* (2006.01)
*B01J 35/10* (2006.01)
*B01J 37/08* (2006.01)
*C07C 35/08* (2006.01)
*C07C 37/01* (2006.01)

(52) U.S. Cl.
CPC ....... *B01J 35/0033* (2013.01); *B01J 35/1038* (2013.01); *B01J 35/1042* (2013.01); *B01J 37/084* (2013.01); *C07C 35/08* (2013.01); *C07C 37/01* (2013.01); *C07C 2521/18* (2013.01); *C07C 2523/44* (2013.01)

(58) Field of Classification Search
CPC ..... B01J 35/1042; B01J 37/084; C07C 35/08; C07C 37/01; C07C 2521/18; C07C 2523/44; C07C 29/145; C01P 2006/10; C01P 2006/11; C01P 2006/40; C01P 2006/72
USPC ....... 502/182, 185; 423/445 R, 447.4–447.5, 423/447.8, 447.9; 585/417–419, 434
See application file for complete search history.

(56) References Cited

U.S. PATENT DOCUMENTS

| | | | | |
|---|---|---|---|---|
| 3,576,767 | A | * | 4/1971 | Summers ................. B01J 23/42 502/185 |
| 3,736,265 | A | * | 5/1973 | Suggitt .................... B01J 27/22 502/185 |
| 3,767,720 | A | * | 10/1973 | Drinkard ................. B01J 23/40 585/267 |
| 4,410,738 | A | | 10/1983 | Cordier |
| 6,066,589 | A | | 5/2000 | Malentacchi et al. |
| 6,114,280 | A | * | 9/2000 | Stephens ............... C01B 32/324 502/437 |
| 2002/0172637 | A1 | * | 11/2002 | Chesneau ............... C02F 1/283 423/445 R |
| 2006/0263288 | A1 | | 11/2006 | Pak et al. |
| 2010/0130788 | A1 | | 5/2010 | Coelho Tsou et al. |
| 2012/0177923 | A1 | * | 7/2012 | Kumara ................ C01B 32/336 428/402 |
| 2014/0287306 | A1 | | 9/2014 | Takeshi et al. |
| 2015/0239743 | A1 | * | 8/2015 | Despen ................... B01J 20/20 210/694 |
| 2015/0357637 | A1 | * | 12/2015 | Yamanoi ............... H01M 4/587 429/231.8 |
| 2016/0028135 | A1 | * | 1/2016 | Iida ........................ H01M 4/96 429/405 |
| 2018/0175439 | A1 | * | 6/2018 | Kang .................... H01M 4/621 |
| 2019/0022624 | A1 | | 1/2019 | Yamanoi et al. |
| 2019/0023578 | A1 | | 1/2019 | Takekuma et al. |
| 2019/0275498 | A1 | * | 9/2019 | Tanba .................... C07C 15/18 |

FOREIGN PATENT DOCUMENTS

| | | | | |
|---|---|---|---|---|
| CN | 112010730 | * | 12/2020 | ............... C07C 1/22 |
| EP | 0879641 | | 11/1998 | |
| GB | 2 269 116 | * | 2/1994 | ........... C07C 29/145 |
| JP | 57-123130 | | 7/1982 | |
| JP | 58026844 | A * | 2/1983 | ............. C07C 87/62 |
| JP | 58-146446 | | 9/1983 | |
| JP | 63096146 | A * | 4/1988 | .............. B01J 23/56 |
| JP | 06-190277 | | 7/1994 | |
| JP | 06-277515 | | 10/1994 | |
| JP | 10-087519 | | 4/1998 | |
| JP | 2006-321712 | | 11/2006 | |
| JP | 2010-526791 | | 8/2010 | |
| JP | 2014-035915 | | 2/2014 | |
| JP | 2017-128497 | | 7/2017 | |
| KR | 2004-0026191 | | 3/2004 | |
| WO | 9747384 | | 12/1997 | |
| WO | 2017146044 | | 8/2017 | |

OTHER PUBLICATIONS

A. Prekob et al., "Hydrogenation of benzophenone by carbon-supported Pd catalysts." Materials Today Chemistry 19, pp. 1-6. (Year: 2021).*
Japanese Office Action dated Dec. 12, 2018 issued in corresponding Japanese application No. 2018-028503.
Japanese Office Action dated Jun. 26, 2019 issued in corresponding Japanese application No. 2018-028503.
International Search Report dated Apr. 23, 2019 issued in the International Patent Application No. PCT/JP2019/002381.
Written Opinion of the International Search Authority dated Apr. 23, 2019 issued in the International Patent Application No. PCT/JP2019/002381.
International Preliminary Report on Patentability dated Mar. 2, 2020 issued in the International Patent Application No. PCT/JP2019/002381.
Extended European Search Report issued in corresponding European Application No. 19757219.1, dated Oct. 22, 2021.
Kania, N. et al., "Scope and limitation of activated carbons in aqueous organometallic catalysis", Journal of Catalysis, vol. 278, No. 2, Dec. 7, 2010, pp. 208-218.
Database WPI Week 201377, Thomson Scientific, London, GB; AN 2013-R13412, XP002804426 (corresponds to CN103121674, previously cited).
Databse WPI Week 199805, Thomson Scientific, London, GB, AN 1998-052073, XP002804442 (corresponds to WO97/47384).

* cited by examiner

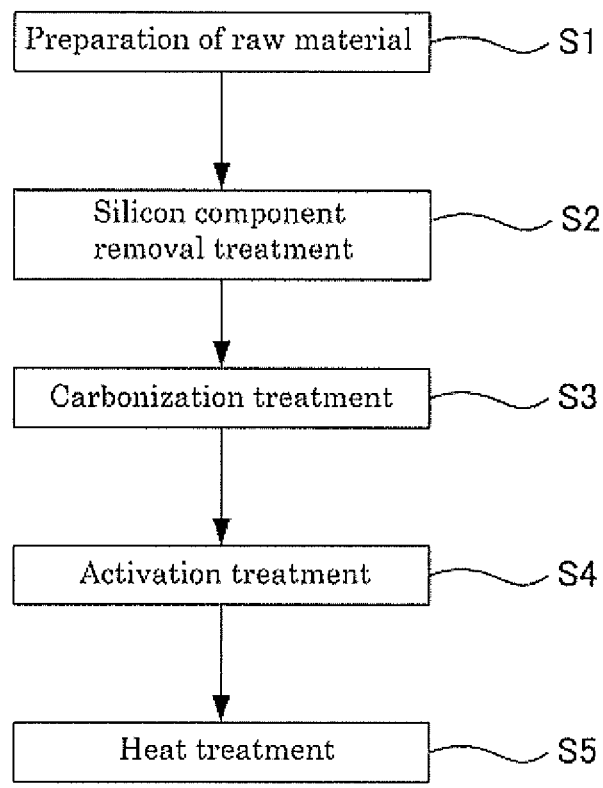

US 11,338,271 B2

POROUS CARBON MATERIAL, METHOD FOR PRODUCING SAME, AND CATALYST FOR SYNTHESIS REACTION

TECHNICAL FIELD

The present invention relates to a porous carbon material, a production method of the porous carbon material, and a catalyst for synthesis reaction.

BACKGROUND ART

A porous carbon material, such as activated carbon, is obtained by treating a carbonized product using a plant-based raw material (e.g., wood pulp, coconut shells, and husks), a mineral-based raw material (e.g., coal, tar, and petroleum pitch), or a synthetic resin as a raw material with gas or a chemical at a high temperature to activate the carbonized product to form pores. The pores are formed inside the carbon in the form of network, and the pores create a large surface area. Therefore, the porous carbon material has an excellent adsorption capacity. For this reason, the porous carbon material has been widely used in various use, such as removal of odor, removal of impurities in a liquid, recovery or removal of solvent vapor, etc.

Other than the use listed above, the porous carbon material is also used as a support for a catalyst. An inhomogeneous catalyst can be obtained by allowing a metal or a metal compound to be supported on the porous carbon material. For example, the activated carbon supporting a metal or a metal compound thereon can be used as a catalyst for synthesis of vinyl acetate or synthesis of vinyl chloride.

Related to a catalyst support that is a porous carbon material, for example, proposed as a catalyst support for a fuel cell electrode is a mesoporous carbon body where surface resistance thereof as measured at pressure of 75.4 kgf/cm$^2$ is 250 mΩ/cm$^2$ or less, and the average diameter of mesopores thereof is from 2 nm to 20 nm (see, for example, PTL 1). Moreover, use of a supported catalyst, in which metal catalyst particles are supported on the catalyst support, for an electrode of a fuel cell has been proposed.

Related to a catalyst for hydrogenation reduction, moreover, proposed as a catalyst capable of carrying out hydrogenation reduction on low reactive ketone is a catalyst composition for hydrogenation including cubic tungsten carbide in the amount of 30% by volume or greater, and at least one of a metal and oxide or carbide (excluding cubic tungsten carbide) of a metal (see, for example, PTL 2).

However, a porous carbon material, which can be used as a support of a supported catalyst effective for hydrogenation reduction of a low-reactive substrate, has not been known. There is therefore a need for a porous carbon material, which can be used as a support of a supported catalyst effective for hydrogenation reduction of a low-reactive substrate.

CITATION LIST

Patent Literature

PTL 1 Japanese Patent Application Laid-Open (JP-A) No. 2006-321712

PTL 2 Japanese Patent Application Laid-Open (JP-A) No. 06-277515

SUMMARY OF INVENTION

Technical Problem

The present invention aims to achieve the following object.

Specifically, the present invention has an object to provide a porous carbon material that can be used as a support for a supported catalyst effective for reduction of a low-reactive substrate, a production method thereof, and a catalyst for synthesis reaction using the porous carbon material.

Solution to Problem

Means for Solving the Above-Described Problems are as Follows

<1> A porous carbon material including:
a porous carbon material having a specific resistance value of 30 Ω·cm or less at a packing density of 0.3 g/cc,
wherein a mesopore volume (cm$^3$/g) of the porous carbon material as measured by BJH method is 0.5 cm$^3$/g or greater.
<2> The porous carbon material according to <1>,
wherein the porous carbon material is derived from a plant.
<3> The porous carbon material according to <1> or <2>,
wherein the porous carbon material is derived from husks.
<4> The porous carbon material according to any one of <1> to <3>,
wherein the porous carbon material is a support for catalyst.
<5> The porous carbon material according to any one of <1> to <4>,
wherein a half width (2θ) of a diffraction peak (10x) (38° to 49°) of the porous carbon material as measured by X-ray diffraction is 4.2° or less.
<6> A catalyst for synthesis reaction, the catalyst including:
the porous carbon material according to any one of <1> to <5>; and
a metal or metal compound that is supported on the porous carbon material.
<7> The catalyst for synthesis reaction according to <6>,
wherein the metal or metal compound is palladium.
<8> The catalyst for synthesis reaction according to <6> or <7>,
wherein the catalyst for synthesis reaction is used for a reduction reaction of a ketone group.
<9> The catalyst for synthesis reaction according to any one of <6> to <8>,
wherein the catalyst of synthesis reaction is used for a reduction reaction of aromatic ketone.
<10> A production method of a porous carbon material, the production method including:
performing an acid treatment or an alkaline treatment to remove a silicon component from a raw material including the silicon component, followed by performing a carbonization treatment,
wherein the production method is a production method of the porous carbon material according to any one of <1> to <5>.
<11> The production method according to <10>, further including:
performing an activation treatment after the carbonization treatment.
<12> The production method according to <11>,
wherein a temperature of the activation treatment is 700° C. or higher but 1,000° C. or lower.

<13> The production method according to <11> or <12>, further including:
performing a heat treatment after the activation treatment.
<14> The production method according to <13>, wherein a temperature of the heat treatment is 800° C. or higher but 2,000° C. or lower.

Advantageous Effects of Invention

The present invention can achieve the above-described object, and can provide a porous carbon material that can be used as a support for a supported catalyst effective for reduction of a low-reactive substrate, a production method thereof, and a catalyst for synthesis reaction using the porous carbon material.

BRIEF DESCRIPTION OF DRAWINGS

FIG. 1 is a flowchart illustrating an example of a production method of a porous carbon material.

DESCRIPTION OF EMBODIMENTS (Porous Carbon Material)

The porous carbon material of the present invention is a porous carbon material having a specific resistance value of 30 Ω·cm or less at a packing density of 0.3 g/cc.

A mesopore volume ($cm^3/g$) of the porous carbon material as measured by the BJH method is 0.5 $cm^3/g$ or greater.

The present inventors have diligently researched on a porous carbon material that can be used as a support for a supported catalyst effective in reduction of a low-reactive substrate.

As a result, it has been found that, by adjusting a specific resistance value and a mesopore volume of a porous carbon material to specific ranges, that is, a specific resistance value at a packing density of 0.3 g/cc being 30 Ω·cm or less, and a mesopore volume ($cm^3/g$) as measured by the BJH method being 0.5 $cm^3/g$ or greater, a supported catalyst using the porous carbon material can perform reduction of a low-reactive substrate at a high reaction rate. The present invention has been accomplished based on the above-mentioned insights.

Specifically, the present inventors prepared a supported palladium catalyst using a porous carbon material whose specific resistance value and mesopore volume are varied, and a hydrogenation reduction reaction of benzophenone to diphenylmethane was performed using the prepared catalyst.

Note that, benzophenone was used as a model compound of a hydrogenation reduction of a low-reactive ketone group.

During the hydrogenation reduction reaction of benzophenone, a hydrogenation reduction reaction of a ketone group to be bonded to a benzene ring occurs. However, reactivity of the ketone group is low.

The present inventors have found that reactivity in the above-mentioned hydrogenation reduction reaction can be improved by adjusting the specific resistance value and mesopore volume of the porous carbon material to the specific ranges.

<Specific Resistance Value>

The specific resistance value of the porous carbon material is 30 Ω·cm or less and more preferably 20 Ω·cm or less at a packing density of 0.3 g/cc. The lower limit of the specific resistance value is not particularly limited and may be appropriately selected depending on the intended purpose. For example, the specific resistance value may be 0.1 Ω·cm or greater, or may be 1 Ω·cm or greater.

When the specific resistance value of the porous carbon material is greater than 30 Ω·cm, reactivity of a supported catalyst using the porous carbon material may be low.

For example, the specific resistance value can be measured by the following method.

An acryl cylinder of 9.0 mm in diameter×17 mm in length is charged with the porous carbon material to achieve the packing density of 0.3 g/cc. Then, a digital multi-meter (VOAC7412, available from IWATSU ELECTRIC CO., LTD.) is connected to the electrodes respectively attached to both ends of the cylinder in the length direction, and the measurement is performed.

The reason why the packing density of the porous carbon material is set to 0.3 g/cc is because the density is 0.3 g/cc when the porous carbon material is moderately packed.

<Mesopore Volume>

The mesopore volume is 0.5 $cm^3/g$ or greater, and preferably 0.6 $cm^3/g$ or greater. The upper limit of the mesopore volume is not particularly limited and may be appropriately selected depending on the intended purpose. For example, the mesopore volume may be 1.5 $cm^3/g$ or less, or may be 1.3 $cm^3/g$ or less.

When the mesopore volume is less than 0.5 $cm^3/g$, reactivity of a supported catalyst using the porous carbon material is low.

The mesopore volume can be measured by the BJH method.

<Half Width>

A half width (2θ) of a diffraction peak (10x) (38° to 49°) of the porous carbon material as measured by X-ray diffraction is preferably 4.2° or less, and more preferably 4.0° or less. The lower limit of the half width is not particularly limited and may be appropriately selected depending on the intended purpose. The half width (2θ) is preferably 3.0° or greater, and more preferably 3.5° or greater.

In the present specification, "10x" denotes a pseudo peak observed adjacent to the (101) plane of graphite.

The X-ray diffraction measurement and the measurement of half width are performed by means of a known X-ray diffraction device. For example, the measurements can be performed by means of PHILIPS X'Pert available from PANalytical.

Examples of a method for adjusting the half width (2θ) to 4.2° or less include a method for performing a heat treatment on a porous carbon material. The heat treatment will be described below.

<Pore Volume>

The porous carbon material includes many pores. The pores are classified into mesopores, micropores, and macropores. The mesopore is a pore having a pore diameter of from 2 nm to 50 nm, the micropore is a pore having a pore diameter of smaller than 2 nm, and the macropore is a pore having a pore diameter of larger than 50 nm.

<<Mesopore Volume>>

The mesopore volume is 0.5 $cm^3/g$ or greater, and preferably 0.6 $cm^3/g$ or greater. The upper limit of the mesopore volume is not particularly limited and may be appropriately selected depending on the intended purpose. For example, the mesopore volume may be 1.5 $cm^3/g$ or less, and may be 1.3 $cm^3/g$ or less.

When the mesopore volume is less than 0.5 $cm^3/g$, reactivity of a supported catalyst using the porous carbon material is low.

The mesopore volume can be measured by the BJH.

For example, the mesopore volume can be measured by means of the following device.

A nitrogen adsorption isotherm is measured by means of a multi-specimen high-performance specific surface area/pore distribution measuring device 3Flex available from Micromeritics Instrument Corp. and the mesopore volume can be calculated according to the BJH method.

The BJH method is a method widely known as a pore distribution analysis method. In the case where pore distribution analysis is performed according to the BJH method, first, nitrogen serving as an adsorption molecule is made adsorbed to or desorbed from a porous carbon material to determine a desorption isotherm. Then, a thickness of an adsorption layer, when the adsorption molecules (e.g., nitrogen) are deposited or desorbed gradually from the state where the pores are filled with the adsorption molecules, and an inner diameter (2 times the radius of the core) of pore after the adsorption are determined based on the determined desorption isotherm, the pore radius $r_p$ is calculated according to the following formula (1), and a pore volume is calculated according to the following formula (2). A pore distribution curve is obtained from the pore radius and pore volume by plotting pore volume change rate ($dV_p/dr_p$) relative to the pore diameter ($2r_p$) (see pages 85 to 88, a manual of BELSORP-mini and BELSORP analysis software available from BEL JAPAN, Inc.).

$$r_p = t + r_k \quad (1)$$

$$V_{pn} = R_n \cdot dV_n - R_n \cdot dt_n \cdot c \cdot \Sigma A_{pj} \quad (2)$$

With the proviso that, $R_n = r_{pn}^2/(r_{kn-1} + dt_n)^2 \quad (3)$

In the formulae above, each term represents as follows.
$r_p$: pore radius
$r_k$: core radius (inner diameter/2) when an adsorption layer having a thickness t is adsorbed on an inner wall of a pore having a pore radius $r_p$ at the pressure
$V_{pn}$: a pore volume when deposition and desorption of nitrogen occurred in the number of "n"
$dV_n$: a change rate thereof
$dt_n$: an amount of change of the adsorption layer when deposition and desorption of nitrogen occurred in the number of "n"
$r_{kn}$: a core radius thereof
c: a fixed value
$r_{pn}$: a pore radius when deposition and desorption of nitrogen occurred in the number of "n"

Moreover, $\Sigma A_{pj}$ is an integrated value of an area of a wall surface of the pore from j=1 to j=n−1.
[Specific Measuring Method of Mesopore Volume]

The porous carbon material (30 mg) was prepared, and a mesopore volume thereof can be measured by means of 3FLEX set to the conditions where the measurement is performed at the relative pressure (P/P0) in the range of from 0.0000001 to 0.995.
<Raw Material of Porous Carbon Material>

A raw material of the porous carbon material is preferably a material derived from a plant. Specifically, the porous carbon material is preferably derived from a plant. Since the raw material is derived from a plant, a mesopore volume value can be easily adjusted to the desired value described above. Another advantage of use of the plant-derived raw material is that environmental load is low.

The material derived from a plant is not particularly limited and may be appropriately selected depending on the intended purpose. Examples of the plant-derived material include: husks and straws of rice (rice plant), barley, wheat, rye, barnyard millet, millet etc.; reeds; and stems of seaweed (*Undaria pionatifida*). Further examples thereof include vascular plants vegetated on the ground, pteridophytes, moss plant, alga, and seaweed. The above-listed material may be used alone or in combination as a raw material. Moreover, a shape or embodiment of the material derived from plant is not particularly limited, and may be, for example, husks or moss itself, or dry-processed products thereof. Moreover, products, to which subjected various treatments in the course of drink and food processing of wines, spirits etc., such as a fermentation treatment, a roasting treatment, and an extraction treatment, may be also used as the material derived from plant. In view of resource recovery of industrial waste, straws or husks obtained after processing, such as threshing, are particularly preferably used. The straws or husks after the processing can be readily available in the large volume, for example, from agricultural cooperatives, breweries and distilleries, and food companies.

Use of the porous carbon material is not particularly limited and may be appropriately selected depending on the intended purpose. Examples thereof include absorbents, and supports for catalyst. Among the above-listed examples, the porous carbon material can be preferably used as a support for catalyst.

A production method of the porous carbon material is not particularly limited and may be appropriately selected depending on the intended purpose. The production method thereof is preferably the below-described production method of the porous carbon material.
(Production Method of Porous Carbon Material)

According to an example of the production method of the porous carbon material of the present invention, an acid treatment or alkaline treatment is performed to remove a silicon component from a raw material including the silicon component, followed by performing a carbonization treatment. Specifically, the example of the production method of the porous carbon material includes a silicon component-removal treatment, and a carbonization treatment in this order.

The production method of the porous carbon material of the present invention includes, for example, a silicon component-removal treatment and a carbonization treatment, and preferably further includes an activation treatment and a heat treatment. The production method may further include other treatments according to the necessity.

The specific resistance value of the porous carbon material can be adjusted by appropriately changing conditions of the carbonization treatment, the activation treatment, the heat treatment, etc.

The production method of the porous carbon material is a production method of the porous carbon material of the present invention.
<Silicon Component-Removal Treatment>

The silicon component-removal treatment is not particularly limited and may be appropriately selected depending on the intended purpose, as long as the silicon component-removal treatment is a treatment including performing an acid treatment or alkaline treatment to remove a silicon component from a raw material including the silicon component. Examples thereof include a method where the raw material is immersed in an acid aqueous solution or alkaline aqueous solution.

Examples of the raw material including the silicon component include a raw material of the porous carbon material described earlier.

Since the silicon component-removal treatment is performed, a mesopore volume or a micropore volume is easily adjusted in the carbonization treatment and activation treatment.

<Carbonization Treatment>

The carbonization treatment is not particularly limited and may be appropriately selected depending on the intended purpose, as long as the carbonization treatment is a treatment that includes carbonizing a raw material on which the silicon component-removal treatment has been performed to obtain a carbonized product (carbonaceous material).

The carbonization typically means that a heat treatment is performed on an organic material (e.g., a plant-based material in the present invention) to convert the organic material into a carbonaceous material (see, for example, JIS M0104-1984). Examples of an atmosphere for carbonization include an oxygen-shielded atmosphere. Specific examples thereof include a vacuum atmosphere, and an inert gas atmosphere, such as nitrogen gas and argon gas. Heating speed until a temperature reaches the carbonization temperature in the above-mentioned atmosphere is 1° C./min or greater, preferably 3° C./min or greater, and more preferably 5° C./min or greater. Moreover, the upper limit of the carbonization time is 10 hours, preferably 7 hours, and more preferably 5 hours, but not limited thereto. The lower limit of the carbonization time is a duration by which the raw material is carbonized completely.

A temperature of the carbonization treatment is not particularly limited and may be appropriately selected depending on the intended purpose. The temperature thereof is preferably 600° C. or higher, and more preferably 600° C. or higher but 1,000° C. or lower.

<Activation Treatment>

The activation treatment is not particularly limited and may be appropriately selected depending on the intended purpose, as long as the activation treatment is a treatment for activating the carbonized product. Examples of the activation treatment include a gas activation method, and a chemical activation method.

The term "activation" means that a pore structure of a carbon material is developed to increase the number of pores.

The gas activation method is a method where the carbonized product is heated using oxygen, water vapor, carbon dioxide, air, etc. as an activator in such an atmosphere, for example, at a temperature of 700° C. or higher but 1,000° C. or lower for several tens minutes to several hours, to thereby develop the pore structure through a volatile component or carbon molecules in the carbonized product. The heating temperature may be appropriately selected depending on a type of a plant-derived material, a type or concentration of gas, etc., but the heating temperature is preferably 750° C. or higher but 1,000° C. or lower.

The chemical activation method is a method where the carbonized product is activated using zinc chloride, iron chloride, calcium phosphate, calcium hydroxide, magnesium carbonate, potassium carbonate, sulfuric acid, etc., instead of oxygen or water vapor used in the gas activation method, the resultant is washed with hydrochloric acid, pH thereof is adjusted with an alkaline aqueous solution, and the resultant is dried.

The duration of the activation treatment is not particularly limited and may be appropriately selected depending on the intended purpose. The duration thereof is preferably 0.5 hours or longer but 20 hours or shorter, and more preferably 1 hour or longer but 10 hours or shorter.

<Heat Treatment>

The heat treatment is not particularly limited and may be appropriately selected depending on the intended purpose, as long as the heat treatment is a treatment configured to heat the carbonized product that has been subjected to the activation treatment. The heat treatment can increase a carbon density of the carbonized product and can improve electrical conductivity of the porous carbon material to be produced.

The temperature of the heat treatment is not particularly limited and may be appropriately selected depending on the intended purpose. The temperature thereof is preferably 800° C. or higher, more preferably 800° C. or higher but 2,500° C. or lower, further more preferably 800° C. or higher but 2,000° C. or lower, and particularly preferably 1,200° C. or higher but 2,000° C. or lower.

The duration of the heat treatment is not particularly limited and may be appropriately selected depending on the intended purpose. The duration thereof is preferably 1 hour or longer but 24 hours or shorter, and more preferably 2 hours or longer but 15 hours or shorter.

The heat treatment is preferably performed in the presence of reducing gas in order to reduce load to a furnace. Examples of the reducing gas include hydrogen gas, carbon monoxide gas, and vapor of organic matter (e.g., methane gas).

The reducing gas is preferably used together with inert gas. Examples of the inert gas include nitrogen gas, helium gas, and argon gas.

An example of the production method of the porous carbon material will be described with reference to FIG. 1.

FIG. 1 is a flowchart illustrating an example of the production method of the porous carbon material.

First, a plant is prepared as a raw material (S1). The plant includes a silicon component.

Subsequently, a silicon component-removal treatment is performed on the raw material using alkali to remove a silicon component from the raw material (S2).

Subsequently, the raw material, from which the silicon component has been removed, is provided to a carbonization treatment (S3). As a result of the carbonization treatment of the raw material, a carbonized product is obtained.

Subsequently, the obtained carbonized product is provided to an activation treatment (S4). As a result of the activation treatment of the carbonized product, a pore structure inside the carbonized product is developed.

Subsequently, the carbonized product which has been subjected to the activation treatment is provided to a heat treatment (S5). As a result of the heat treatment of the carbonized product, a carbon density of the carbonized product is increased to improve electrical conductivity.

In the manner as described above, a porous carbon material is obtained.

(Catalyst for Synthesis Reaction)

The catalyst for a synthesis reaction of the present invention includes the porous carbon material of the present invention, and a metal or a metal compound supported on the porous carbon material. The catalyst may further include other components according to the necessity.

The metal is not particularly limited and may be appropriately selected depending on the intended purpose, as long as the metal is a catalytic active ingredient. Examples of the metal include platinum group elements (platinum, iridium, osmium, ruthenium, rhodium, and palladium), rhenium, gold, and silver.

The metal compound is not particularly limited and may be appropriately selected depending on the intended purpose, as long as the metal compound is a catalytic active ingredient. Examples thereof include alloys the above-listed metals.

Among the above-listed examples, the metal or the metal compound is preferably palladium because of price and availability thereof.

Examples of a method for allowing the metal or the metal compound to be supported on the porous carbon material include the following methods.

(1) A method where the porous carbon material that is a catalyst support is dispersed in a solution of a metal that is a catalytic active ingredient, a reducing agent is further added to the dispersion, and the metal is deposited on the porous carbon material that is the catalyst support.

(2) A method where a solution of a metal that is a catalytic active ingredient, in which the porous carbon material that is a catalyst support is dispersed, is heated and stirred to deposit the catalytic active ingredient on the catalyst support, followed by optionally performing filtration, washing, and drying, and performing a reduction treatment with hydrogen gas etc.

A ratio between the porous carbon material and the metal or metal compound in the catalyst for synthesis reaction is not particularly limited and may be appropriately selected depending on the intended purpose.

The catalyst for synthesis reaction can be suitably used for a reduction reaction of a ketone group. Moreover, the catalyst for synthesis reaction can be more suitably used for a reduction reaction of aromatic ketone. In the present specification, the "aromatic ketone" means a compound in which a ketone group is bonded to an aromatic ring.

(Synthesis Method of Compound)

A synthesis method of a compound of the present invention includes at least a reduction step. The synthesis method may further include other steps according to the necessity.

<Reduction Step>

The reduction step is not particularly limited and may be appropriately selected depending on the intended purpose, as long as the reduction step is a step including reducing a compound using the catalyst for a synthesis reaction of the present invention.

The compound is not particularly limited and may be appropriately selected depending on the intended purpose, as long as the compound is a compound including a group that can be reduced. The compound is preferably a compound including a ketone group, and more preferably aromatic ketone. In the present specification, the aromatic ketone means a compound in which a ketone group is bonded to an aromatic ring.

An amount of the catalyst for a synthesis reaction used in the synthesis reaction of the compound is not particularly limited and may be appropriately selected depending on the intended purpose. The amount thereof is preferably 0.5 parts by mass or greater but 5.0 parts by mass or less, and more preferably 2.0 parts by mass or greater but 4.0 parts by mass or less, relative to 100 parts by mass of the compound.

In the course of the synthesis method of the compound, heating may be performed, or a reaction may be performed at room temperature.

The synthesis method of the compound is preferably performed in the presence of reducing gas. Examples of the reducing gas include hydrogen gas, carbon monoxide gas, and vapor of organic matter (e.g., methane gas).

EXAMPLES

Examples of the present invention will be described hereinafter. However, these examples shall not be construed as to limit the scope of the present invention.

<Raw Material>

As a raw material, husks produced in Miyagi Prefecture, Japan were used.

<Alkaline Treatment>

An alkaline treatment (silicon component-removal treatment) for removing a silicon component was performed by immersing the husks in a 5.3% by mass sodium hydroxide aqueous solution at 90° C. for 14 hours.

<Carbonization Treatment>

A carbonization treatment was performed by a carbonization furnace in a nitrogen atmosphere ($N_2$=30 L/min) at 600° C. for a predetermined duration.

<Activation Treatment>

An activation treatment was performed with water vapor by a rotary kiln under nitrogen bubbling ($N_2$=10 L/min) at a predetermined temperature for a predetermined duration.

<Heat Treatment>

A heat treatment was performed with supplying argon gas (2.5 L/min), at a predetermined temperature for a predetermined duration.

Examples 1 to 4

As treatments performed on husks, the alkaline treatment, the carbonization treatment, the activation treatment, and the heat treatment were performed in this order under the conditions presented in Table 1, to thereby obtain a porous carbon material.

Comparative Example 1

As treatments performed on husks, the alkaline treatment and the carbonization treatment were performed in this order under the conditions presented in Table 1, to thereby obtain a porous carbon material.

Comparative Examples 2 and 3

As treatments performed on husks, the alkaline treatment, the carbonization treatment, and the activation treatment were performed in this order under the conditions presented in Table 1, to thereby obtain a porous carbon material.

Comparative Example 4

As treatments performed on husks, the alkaline treatment, the carbonization treatment, and the heat treatment were performed in this order under the conditions presented in Table 1, to thereby obtain a porous carbon material.

The obtained porous carbon materials were subjected to the following evaluations.

<Measurement of Specific Resistance Value>

The specific resistance value of the porous carbon material was measured by the following method.

An acryl cylinder of 9.0 mm in diameter×17 mm in length was charged with the porous carbon material to achieve the packing density of 0.3 g/cc. Then, a digital multi-meter (VOAC7412, available from IWATSU ELECTRIC CO., LTD.) was connected to the electrodes respectively attached to both ends of the cylinder in the length direction, and the measurement was performed. The results are presented in Table 2.

<Half Width>

For a measurement of a half width (2θ) of (10x) (38° to 49°) by X-ray diffraction, PHILIPS X'Pert available from PANalytical was used. The results are presented in Table 2.

<Mesopore Volume>

For a measurement of a mesopore volume, a multi-specimen high-performance specific surface area/pore distribution measuring device 3Flex available from Micromeritics Instrument Corp. was used. The result is presented in Table 2.

<Catalytic Performance>
<<Production of Palladium Carbon Catalyst>>

The porous carbon material was immersed in a hydrochloric acid solution, which had been adjusted to achieve 5% by mass of the Pd metal relative to 1 g of the porous carbon material. Thereafter, the porous carbon material was vacuum dried at 100° C. for 2 hours. Moreover, a reduction treatment was performed in a hydrogen-containing gas atmosphere at 400° C. for 3 hours. As a result, a palladium carbon catalyst where the palladium was supported on the porous carbon material was obtained.

<<Synthesis of Diphenylmethane>>

A 10 mL-test tube was charged with the following composition, and a hydrogenation reaction was carried out with stirring at 500 rpm for 8 hours while supplying hydrogen gas with a balloon.

The main product was diphenylmethane, and the reaction yield was calculated based on the generated amount relative to the charged amount of benzophenone. The reaction yield was determined by means of Agilent 6890N/5975MSD (GC/MS).

[Composition]
Benzophenone 44.5 mg
Palladium/carbon catalyst: 1.3 mg
Deuterated methanol as a solvent: 1 mL

TABLE 1

| | | | Production method | | | | | |
|---|---|---|---|---|---|---|---|---|
| | | | Carbonization Treatment | | Activation treatment | | Heat treatment (Ar atmosphere) | |
| Item | Raw material | Alkali treatment | Temperature ° C. | Time Hr | Temperature ° C. | Time Hr | Temperature ° C. | Time Hr |
| Ex. 1 | Husks | Performed | 600 | 3 | 950 | 8 | 1200 | 10 |
| Ex. 2 | | | | | 950 | 8 | 1500 | 10 |
| Ex. 3 | | | | | 950 | 8 | 2000 | 10 |
| Ex. 4 | | | | | 950 | 8 | 1500 | 3 |
| Comp. Ex. 1 | | | | 6 | — | — | — | — |
| Comp. Ex. 2 | | | | 3 | 750 | 3 | — | — |
| Comp. Ex. 3 | | | | | 950 | 3 | — | — |
| Comp. Ex. 4 | | | | 6 | — | — | 1500 | 10 |

TABLE 2

| | Specific resistance value ($\Omega \cdot$ cm) | Mesopore volume (cm$^3$/g) | Half width (°) of (10X) 38° to 49° |
|---|---|---|---|
| Ex. 1 | 9.7 | 1.12 | 4.0 |
| Ex. 2 | 4.0 | 0.97 | 3.7 |
| Ex. 3 | 2.5 | 0.80 | 3.3 |
| Ex. 4 | 26.1 | 1.02 | 4.1 |
| Comp. Ex. 1 | 6.9 × 10$^6$ | 0.10 | —* |
| Comp. Ex. 2 | 4.9 × 10$^4$ | 0.26 | 5.6 |
| Comp. Ex. 3 | 38.4 | 0.50 | 4.7 |
| Comp. Ex. 4 | 3.9 | 0.19 | 3.9 |

Note that, "*" means that the result was equal to or lower than the detection limit.

TABLE 3

| | Amount of diphenylmethane generated (%) |
|---|---|
| Ex. 1 | 46.3 |
| Ex. 2 | 60.9 |
| Ex. 3 | 51.4 |
| Ex. 4 | 40.3 |
| Comp. Ex. 1 | 4.7 |
| Comp. Ex. 2 | 2.3 |
| Comp. Ex. 3 | 6.8 |
| Comp. Ex. 4 | 15.1 |

The porous carbon materials produced in Examples 1 to 4 had excellent catalytic performance when the porous carbon materials were used as a catalyst, compared to the porous carbon materials produced in Comparative Examples 1 to 4.

Specifically, the porous carbon material, which had the specific resistance value of 30 $\Omega \cdot$cm or less at the packing density of 0.3 g/cc and had a mesopore volume (cm$^3$/g) of 0.5 cm$^3$/g or greater as measured by the BJH method, had excellent catalytic performance.

When the specific resistance value was greater than 30 $\Omega \cdot$cm, the reactivity was low (Comparative Examples 1 to 3).

When the mesopore volume was less than 0.5 cm$^3$/g, the reactivity was low (Comparative Examples 1, 2, and 4).

INDUSTRIAL APPLICABILITY

The porous carbon material of the present invention can be suitably used as a support for catalyst, etc.

The invention claimed is:

1. A catalyst for synthesis reaction, the catalyst comprising:
   a porous carbon material that is derived from husks, and
   a metal or metal compound that is supported on the porous carbon material,
   the porous carbon material having a specific resistance value of 30 $\Omega \cdot$cm or less at a packing density of 0.3 g/cc, and
   wherein a mesopore volume (cm$^3$/g) of the porous carbon material as measured by BJH method is 0.5 cm$^3$ or greater.

2. The catalyst for synthesis reaction according to claim 1, wherein the metal or metal compound is palladium.

3. The catalyst for synthesis reaction according to claim 1, wherein the catalyst for synthesis reaction is used for a reduction reaction of a ketone group.

4. The catalyst for synthesis reaction according to claim 1, wherein the catalyst of synthesis reaction is used for a reduction reaction of aromatic ketone.

5. The catalyst for synthesis reaction according to claim 1, wherein the porous carbon material has a specific resistance value of 2.5 Ω·cm or greater at a packing density of 0.3 g/cc.

6. A production method of a catalyst or synthesis reaction, the production method comprising:
   performing an acid treatment or an alkaline treatment to remove a silicon component from a raw material including the silicon component, followed by performing a carbonization treatment,
   wherein the production method is a production method of the catalyst for synthesis reaction according to claim 1.

7. The production method according to claim 6, further comprising:
   performing an activation treatment after the carbonization treatment.

8. The production method according to claim 7, wherein a temperature of the activation treatment is 700° C. or higher but 1,000° C. or lower.

9. The production method according to claim 7, further comprising:
   performing a heat treatment after the activation treatment.

10. The production method according to claim 9, wherein a temperature of the heat treatment is 800° C. or higher but 2,000° C. or lower.

\* \* \* \* \*